United States Patent
Clupper et al.

(10) Patent No.: US 6,306,925 B1
(45) Date of Patent: Oct. 23, 2001

(54) TAPE CAST MULTI-LAYER CERAMIC/METAL COMPOSITES

(75) Inventors: Daniel Clupper; John J. Mechlosky, Jr., both of Gainesville, FL (US); Zheng Chen, Auburn, AL (US)

(73) Assignee: Usbiomaterials Corporation, Alachua, FL (US)

( * ) Notice: Subject to any disclaimer, the term of this patent is extended or adjusted under 35 U.S.C. 154(b) by 0 days.

(21) Appl. No.: 09/216,510

(22) Filed: Dec. 18, 1998

Related U.S. Application Data

(60) Provisional application No. 60/068,174, filed on Dec. 19, 1997.

(51) Int. Cl.$^7$ ............... A61F 2/28; A61F 2/02; B32B 15/18
(52) U.S. Cl. ............ 523/113; 106/35; 428/469; 428/472.2; 428/472.1; 428/472; 428/471; 428/689; 428/701; 523/114; 523/115; 623/11; 623/16
(58) Field of Search ................. 523/113, 114, 523/115; 428/469, 472.2, 472, 471, 472.1, 689; 623/11, 16; 106/35

(56) References Cited

U.S. PATENT DOCUMENTS

| | | | |
|---|---|---|---|
| 4,159,358 | 6/1979 | Hench et al. | 427/318 |
| 4,613,516 * | 9/1986 | Kucheria et al. | 427/2.27 |
| 4,652,459 * | 3/1987 | Engelhardt | 427/2.27 |
| 4,775,646 | 10/1988 | Hench et al. | 623/23.61 |
| 5,017,627 | 5/1991 | Bonfield et al. | 523/115 |
| 5,139,424 | 8/1992 | Yli-Urpo | 433/201.1 |
| 5,145,520 | 9/1992 | Kokubo et al. | 106/35 |
| 5,204,106 | 4/1993 | Schepers et al. | 424/423 |
| 5,236,458 | 8/1993 | Ducheyne et al. | 623/23.56 |
| 5,480,438 * | 1/1996 | Arima et al. | 623/16 |
| 5,645,934 | 7/1997 | Marcolongo et al. | 523/114 |
| 5,681,872 | 10/1997 | Erbe | 523/114 |
| 5,728,753 | 3/1998 | Bonfield et al. | 523/114 |

OTHER PUBLICATIONS

Kokubo, T., et al., "Solutions able to reproduce in vivo surface–structure changes in bioactive glass–ceramic A–W$^3$", *J. Biomed. Mater. Res.*, 24, p721–734, 1990.
**Filho, O.P., et al., "Effect of Crystallization on apatite–layer formation bioactive glass 45S5," *J. Biomed. Mater. Res.*, 30, 509–514, 1996.
**Reed, James S., "Principles of Ceramics Processing," *J. Wiley and Sons, Inc.*, 1995.

* cited by examiner

*Primary Examiner*—Peter Szekely
(74) *Attorney, Agent, or Firm*—Burns, Doane, Swecker & Mathis, L.L.P.

(57) ABSTRACT

The invention described herein is a bioactive composite material comprising thin layers of bioactive glass reinforced with thin ductile metallic layers, and the use of this material in bone replacement procedures.

12 Claims, 3 Drawing Sheets

Reproduction of a FTIR spectra for sintered (1000°C) 45S5 Bioglass (brand of bioactive glass) discs unreacted

TAPE CAST MULTI-LAYER CERAMIC/METAL COMPOSITES

This application claims benefit of Prov. No. 60/068,174 filed Dec. 19, 1997.

BACKGROUND OF THE INVENTION

Natural (autogenic and allogenic) bone tissue is commonly used for bone replacement to correct defects caused by disease or trauma. However, natural bone tissue is not available in sufficient quantities to meet the growing demand. Further, there is a risk of viral infection associated with the use of transplanted tissue. Synthetic materials currently available are limited by inadequate mechanical properties, poor implant-tissue interfacial bonding, or both. Initial implant stability is enhanced if the implant is able to rapidly bond to the surrounding tissue. New orthopaedic synthetic biologically active materials are needed which are readily available and have bonding and mechanical properties comparable to that of natural bone tissue.

The major mineral phase in bone, hydroxyapatite ("HA"), which has the chemical formula: $Ca_{10}(PO_4)_6(OH)_2$, is able to slowly bond with bone in vivo. By contrast, the inert metals, such as stainless steel and titanium, used in the construction of implanted orthopaedic devices are not generally considered to bond to bone or soft tissue and are generally attached by mechanical means such as pins and screws. In many cases, it would be desirable for the devices to bond to body tissue. That is, material from which the devices were constructed should be biologically active, i.e. "bioactive." Thus, researchers have focused on developing HA coatings for orthopaedic implants which would allow the implants to become bound to body tissue. Unfortunately, the bond which forms between HA and metal implants is weak and subject to fracture. Also, the long term effects of HA coatings relative to uncoated, mechanically bound prostheses are unknown.

The bioactivity index is a measure of the time required for greater than 50% of the interface of a material with bone to become bonded to the bone. The bioactivity index of hydroxyapatite is 3.1. In comparison, the indexes for certain biologically active glasses composed of $SiO_2$, $Na_2O$, $CaO$ and $P_2O_5$, "bioactive glasses" as they are known, are significantly higher. For example, for the particular bioactive glass, 45S5 BIOGLASS®, the index is reported to be 12.5. Bioactive glasses when exposed to aqueous solution, e.g., simulated body fluid or water, the outer silica layer becomes hydrated and serves as a nucleation site for precipitation of amorphous calcium phosphate, which becomes crystalline with time. Silicon ions released form the hydrated layer appear to enhance the proliferation of osteoblasts, the cells which build bone. Thus, when immobilized against bone for two weeks 45S5 BIOGLASS® forms an interfacial bond as strong as the bone itself. [Filho, O. P. LaTorre, G. P. and Hench, L. L. (1996). "Effect of Crystallization on apatite-layer formation bioactive glass 45S5, J. Biom. Mater. Res. 30, 509–514.]

Although bioactive glass has a significant advantage over hydroxyapatite because it is able to rapidly bond to bone and soft tissue, its mechanical properties are insufficient to allow it to be used for load-bearing applications including use as a bonding medium for implants and for extensive bone replacement. For example, researchers have attempted to coat metallic implants with bioactive glass in efforts to impart the surface with the ability to bond with bone and surrounding tissue. However, the metal-glass bond was not strong enough to be practical. Thus, significant improvement of the mechanical properties of bioactive glasses was needed to meet the demands of load bearing applications.

Attempts to produce laminate composites with (a) high strain to failure and (b) a bioactive coating have been disappointing. Development of a bioactive laminate with flexural strength (100 MPa) and strain to failure equal to that of bone (8%) would be of clinical significance.

The use of bioactive ceramics and glass in polymer composites is known in the art (see, for example, U.S. Pat. Nos. 5,017,627 and 5,728,753 to Bonfield et al.). These patents teach the use of a dispersed phase of a bioactive material, either bioactive glass, or hydroxyapatite, in a polyolefinic matrix. These materials are limited in their ultimate tensile strength, and do not possess the fracture toughness necessary to be a fully weight-bearing bone implant. The dispersed phase, whether a particulate or a fiber, can act as a stress-riser, which limits the usful mechanical properties of the material. In addition, they only have a percentage of bioactive material at their surface. It would be advantageous to provide materials with a bioactive surface which increases the bone and soft tissue bonding ability of the material, while gaining significant tensile strength properties and fracture toughness higher than conventional bioactive composite materials.

SUMMARY OF THE INVENTION

An aspect of the present invention is a bioactive bone replacement composite material comprising bioactive glass reinforced with one or more ductile metallic layers. Preferably, the composite includes at least two ductile metallic layers and has a flexural strength equal to or greater than 100 MPa and fracture toughness of greater than 5 MPa $m^{1/2}$ and the metallic layer is a corrosion resistant metal such as stainless steel or titanium. The metal can also be, for example, titanium alloys, cobalt, chrome, cobalt-chrome alloys, nickel or aluminum. It is also preferable that the material be in the form of a tape and that alumina be incorporated into at least one layer of the tape to provide a layer with high wear resistance. Several layers of bioactive material in the form of thin tapes may be bonded together. Another aspect of the present invention is the use of the material described above in bone replacement procedures. The present invention is further directed to a process for making such compositions.

DETAILED DESCRIPTION OF THE INVENTION

Figure 1A:
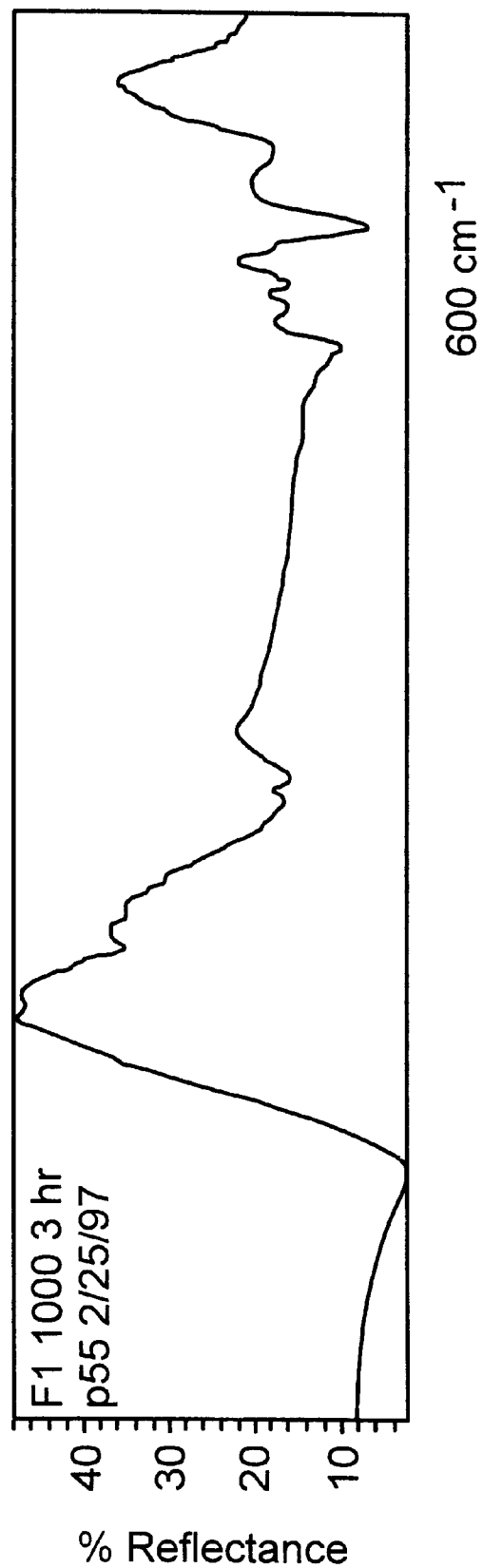
FIG. 1. Reproduction of a FTIR spectra for sintered (1000° C.) 45S5 BIOGLASS® (brand of bioactive glass) discs: (a) unreacted and (b) reacted for 24 hours.

Bioactive glasses in accordance with the present invention are any glasses capable of forming hydroxycarbonate apatite (HCA) after exposure to simulated body fluids. Bioactive glasses include but are not limited to melt-derived, ceramic, and sol-gel bioactive glasses. For example, such glasses may have the following compositional ranges:

| | |
|---|---|
| SiO₂ | 40–60 |
| CaO | 10–30 |
| Na₂O | 10–35 |
| P₂O₅ | 2–8 |
| CaF₂ | 0–25 |
| B₂O₃ | 0–10 |
| K₂O | 0–8 |
| MgO | 0–5 |

The preferred composition of the bioactive glass (BIOGLASS®) is:

| | |
|---|---|
| SiO₂ | 45 |
| CaO | 24.5 |
| Na₂O | 24.5 |
| P₂O₅ | 6 |

Metallic layers in accordance with the present invention may include all metals typically used in biological applications such as titanium, titanium alloys, stainless steel, cobalt, chrome, cobalt-chrome alloys, aluminum, or nickel.

Tapes of bioactive glass in accordance with the present invention may be formed by casting. In the tape casting process, fine particles (typically 0.5–2.0 microns as measured by SEM or laser light scattering techniques) of bioactive glass, organic binder and plasticizers and dispersants are mixed to form a homogeneous slurry. The slurry is then poured onto a moving carrier film (i.e., polypropylene), forming a flexible tape by means of a doctor blade. The organic binder and plasticizer impart the tape with strength and flexibility. After drying, tapes of roughly 100 microns thickness are then peeled from the carrier film and laminated with tapes of similar or different composition to form a multi-layer bioactive material. Organic compounds are then removed prior to sintering. Addition of a thin, reinforcing, metallic layer significantly improves the mechanical properties of multi-layer, bioactive materials.

A process in accordance with the present invention incorporates a metal layer into a bioactive multi-layer. This may be accomplished with tape cast technology. The bioactive layers may be tape cast and then the metal layers, or thin metal foils are laminated to the bioactive layer(s) in the proper location for maximum toughness and strength. The thickness of the metal layers should be at least 50 microns and are typically no more than 200 microns. The metallic layers should remain ductile, i.e., retain a strain-to-failure rate greater than about 3–8% at body temperatures. The layer should be near the surface in order to act as a crack arrestor. The outer layer can be any bioactive glass material. The interlayers, which include metal and ceramic powders, are designed to produce an interface between the metal and bioactive layer which can be smooth, tortuous or intermediate between the two extremes in tortuosity.

Advantages of the present invention include the variation of the thickness and number of the metal layers, the method of bonding of the metal layer to the bioactive layer, the location of the metal layer with respect to the surface and the selection of the materials. This process has been designed for a broad range of materials. Any two chemically compatible bioactive/metal materials may be used. Preferably, bioactive glass is the outer layer and a metal layer preferably includes titanium, stainless steel, aluminum or nickel. The subsurface layers can also be alumina, porous hydroxyapatite, zirconia, metal, porous alumina or any other compatible, desired materials. Such composite material would have wide application in reconstructive surgery, especially where bone replacement is indicated.

Ideally, the mechanical properties of the composite would match those of natural bone. Table I includes the mechanical properties of cortical bone. Metal layer reinforcement provides the added strength and toughness necessary to match the flexural strength and strain to failure of bone. Metal selection involves the consideration of the conventional metals used as orthopaedic biomaterials, thermal expansion, oxidation stability, ability to be processed concurrently with bioactive glass, and availability. Table II lists the deciding factors for each metal system.

TABLE I

Mechanical Properties of Cortical Bone

| | |
|---|---|
| Young's Modulus | 6–20 GPa |
| Flexural Strength | 100–200 MPa |
| Fracture Toughness | 2–12 MPa m$^{1/2}$ |
| Strain to Failure | 8% |

TABLE II

Reasons for Selecting Metal Systems

| Stainless Steel (316L) | Titanium |
|---|---|
| Orthopaedic material | Orthopaedic material |
| Relative oxidation resistance | Biocompatibility |
| Thermal expansion greater than bioactive layer | |
| flakes commercially available | 2 μm Powder available |

Tape casting is a method that has been used commercially for the production of ceramic sheets for use in multilayer capacitors and substrates. It is currently being investigated as a method for producing structural ceramics because the individual lamina are thin and hence, the maximum flaw size is only as large as the tape thickness. These advantages, along with the possibility of producing complex shapes, make tape casting an attractive method for producing structural, bioactive material composites.

In the tape casting process, fine particles (preferably 0.5–2.0 microns) of bioactive glass, organic binder and plasticizers and dispersants are mixed to form a homogeneous slurry. Both attritor milling (4 hours, 400 rpm) and ball milling (16 hours) are sufficient to reduce the initial bioactive glass particle size to that sufficient for tape casting. It is known in the art that the quality and mechanical properties of sintered ceramics are influenced by the degree of homogeneity of the starting powders. [Reed, James S., Principles of Ceramics Processing, J. Wiley and Sons, Inc., NY, 1995.] The slurry is then poured onto a moving carrier film (i.e. polypropylene), forming a flexible tape by means of a doctor blade. The organic binder and plasticizer impart the tape with strength and flexibility. After drying, tapes of about 100 microns thickness are then peeled from the carrier film and laminated with tapes of similar or different composition. Organic compounds are then removed prior to sintering.

Preparation of Composite Material
Preparation of the Bioactive Glass Slurry

Powdered bioactive glass, such as 45S5 BIOGLASS® (<125 μgm) commercially available from U.S. Biomaterials Alachua, Fla., is milled using 3–4 mm ZrO₂ media in denatured ethanol to a particle size distribution amenable to tape casting (0.2–20 μm). Slurries of bioactive glass are prepared by dissolving a polymer binder, e.g., polyvinylbutyral, and a plasticizer, e.g., phthalic acid, in a suitable solvent, preferably a polar, protic solvent, e.g., an alcohol, an ester, an aromatic solvent, or mixtures thereof, such as 20% ethanol/80% toluene by weight. The bioactive glass powder and $ZrO_2$ milling media are added and the slurry is mixed, e.g. for 12 hours. Table III shows the specific amount of each material to be used in the formation of the tape casting slurries.

TABLE III

Standard Formula for Tape Cast Slurries

| Component | Chemical | Weight % (Slurry) |
|---|---|---|
| Powder | BIOGLASS ®, Ti, or 316L, or Ti alloy or Co—Cr | 20–80 |
| Binder | Polyvinylbutyral (PVB) | 2–12 |
| Plasticizer | Phthalic acid | 0–6 |
| Solvent | Toluene/ethanol | 30–70 |

After mixing, the slurries are allowed to settle for about 15 minutes to allow air bubbles to escape prior to casting. Typically, tapes are cast at a rate of about 1.0 ft/min to about 3.0 ft/min, e.g., 2.6 ft/min. Metal tapes and BIOGLASS®-metal tape preparation is carried out in the same manner as described above.

It is desirable to have the maximum amount of powder in the slurry to achieve close packing of the glass or metal particles which will allow more complete sintering. However, the viscosity of the slurry must be sufficient for casting. Thinner tapes are also desirable so that the largest flaws are relatively small. Therefore, the slurry composition is optimized to achieve these goals.

Lamination

Circular shapes cut from the tapes (1–25" diameter by about 100 μm thick) are stacked and cold pressed from to about 20 to 250 MPa and 75°–200° C. for 10 to 15 minutes. A functionally gradient material can then be formed using tapes containing mixtures of bioactive glass and metal powder. For example, the composite may include a titanium inner layer surrounded by 50/50 bioactive glass layers and covered with pure bioactive glass surface layers. The interlayers between the metal and BIOGLASS® can be a mixture of the two materials in order to control the geometry and thermal expansion coefficient of the interface.

Binder Removal

Organic binding material can be removed between about 450° C. and about 600° C. [Reed, James S., Principles of Ceramics Processing, J. Wiley and Sons, Inc., NY, 1995.] Although a rapid burnout schedule is desired for economic reasons, slow burnout is more like to remove organics homogeneously. The resulting powder compact is fairly fragile.

Differential thermal analysis (DTA) and thermogravimetric analysis (TGA) have shown that burnout is complete for an alumina tape between 487.5–535° C. using a 10° C./min heating rate. This value will decrease slightly at for the rate used for burnout (1° C./min). Organic materials can be removed from 316L stainless steel laminates without excessive oxidation occurring. Titanium is less oxidation resistant, but reduction in $H_2$ atmosphere is possible during hot pressing.

Sintering/Hot Pressing

Laminates may be hot pressed under vacuum or under specific (typically inert) atmosphere or sintered without pressure in air. Hot pressed samples are processed in vacuum or under atmosphere using a die, e.g. graphite, and at a typical temperature and pressure of 1350° C. and 46 MPa, respectively. During hot pressing, samples are covered with graphite or tantalum sheets. During the first stage of hot pressing a reducing atmosphere (4% $H_2$/Ar) may be introduced to remove any oxide which forms during binder removal.

Air-sintered samples may be processed in a furnace such as a Thermolyne (FA 1730) furnace (maximum operating temperature of 1093° C.) or its equivalent. A schedule for bioactive glass, e.g., 45S5 BIOGLASS®, processing is shown in Table VI.

TABLE VI

Sintering Schedule

| Stage | Rate (° C./min) | Plateau Temp (° C.) | Hold (min) |
|---|---|---|---|
| 1 | 1 | 1000 | 180 |
| 2 | 1 | 25 | end |

The glass transition temperature of bulk 45S5 BIOGLASS® is approximately 550° C. and wetting occurs near 900° C. Differential thermal analysis (DTA) may be used to compare these values with those of particulate 45S5 BIOGLASS® to assess the crystallization kinetics which are useful in determining the hot press heating schedule.

Densification

Only minimal densification of ball milled bioactive glass (5–50 microns) occurs between 600° C. to 700° C. For good consolidation, the bioactive glass must be processed at 80° C. or above. For example, 45S5 BIOGLASS® tape thickness decreases by approximately 55% after burnout and sintering.

Bioactive glass discs pressureless-sintered in air between 900° to 1000° C. undergo significant crystallization. Samples subsequently hot pressed in vacuum ($<10^{-3}$ torr) at 1000° C. for two hours at 30 MPa do not experience further shrinkage or densification.

Thus, the bioactive glass in its as-laminated, amorphous form will have, at elevated temperature, a viscosity too low to be sintered concurrently with titanium and 316L stainless steel powder. Therefore (a) the bioactive glass composite must be held at elevated temperatures, e.g., 800–1000° C. during hot pressing under vacuum to allow for crystallization prior to application of pressure during consolidation of the metal phase or (b) the bioactive glass layer must be sintered alone prior to hot pressing to induce adequate crystallization so that it is unable to flow at the metal processing temperature and pressure or (c) the milled bioactive glass powder must be crystallized prior to tape casting.

Bioactivity

The bioactivity, i.e., the ability to chemically bond to both bone and soft tissue, was assessed in vitro by soaking the laminate composite material in simulated body fluid (SBF) followed by FTIR spectroscopic analysis to determine the extent of hydroxyapatite formation on the bioactive glass surface. The SBF can be prepared by mixing sodium chloride, sodium bicarbonate, potassium chloride, calcium chloride, dibasic potassium phosphate and magnesium chloride in de-ionized water [Filho, O. P. LaTorre, G. P. and Hench, L. L. (1996). "Effect of Crystallization on apatite-layer formation bioactive glass 45S5, J. Biom. Mater. Res. 30, 509–514. Kokubo,T, Kushitani, H., Sakka, S. Kitsugi, T., and Yamamuro, T. (1990). "Solutions able to reproduce in vitro surface-structure changes in bioactive glass-ceramic A–W," J. Biomed. Mater. Res. 24, 721–34.]

Table VII compares the ionic concentrations of SBF with that of blood plasma.

TABLE VII

Comparison of Ionic Concentrations of SBF and Blood Plasma (mM)

| Ion | SBF | Blood Plasmas |
| --- | --- | --- |
| $Na^+$ | 142.0 | 142.0 |
| $K^+$ | 5.0 | 5.0 |
| $Mg^{2+}$ | 1.5 | 1.5 |
| $Ca^{2+}$ | 2.5 | 2.5 |
| $Cl^-$ | 147.8 | 103.0 |
| $HCO_3^-$ | 4.2 | 27.0 |
| $HPO_4^{2-}$ | 1.0 | 1.0 |
| $SO_4^{2-}$ | 0.5 | 0.5 |

Specifically, disks (1.1 cm diameter by 2–3 min thick) of the sintered bioactive glass laminates to be tested are immersed 25.0 mL SBF preheated to 37° C. Typically, the disks are hung in the center of a 30 mL polyethylene bottle, or similar container, to maximize the available surface area. Tests are conducted after immersion from about 2 hours to 8 weeks of immersion.

Figure 1B:
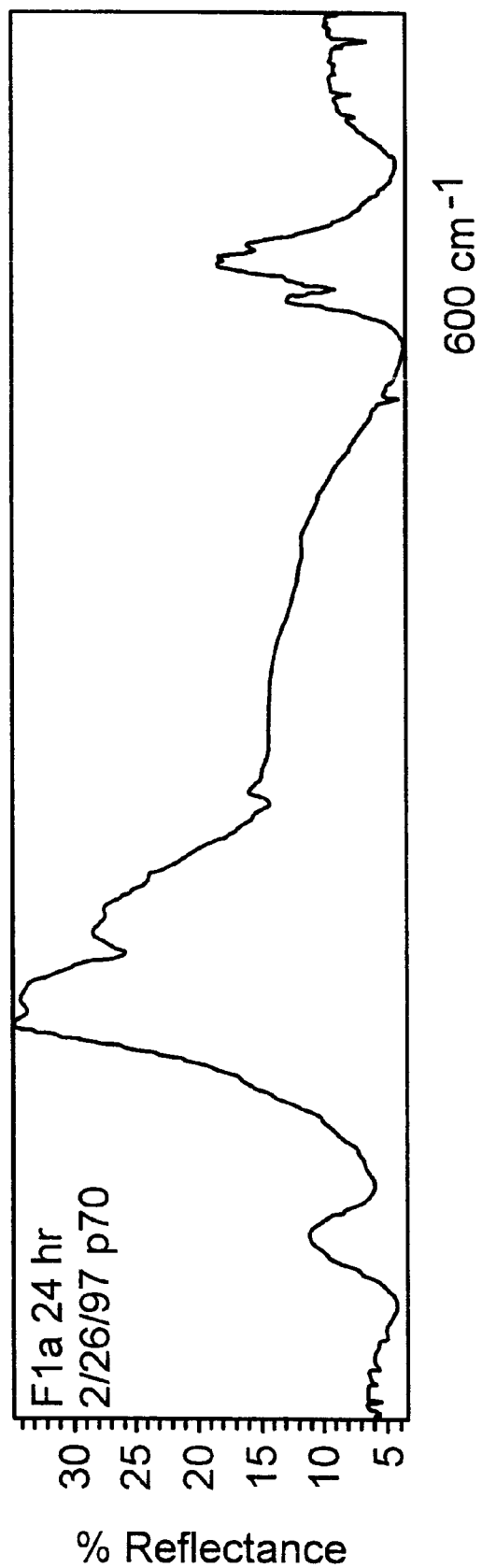
Figure 2:
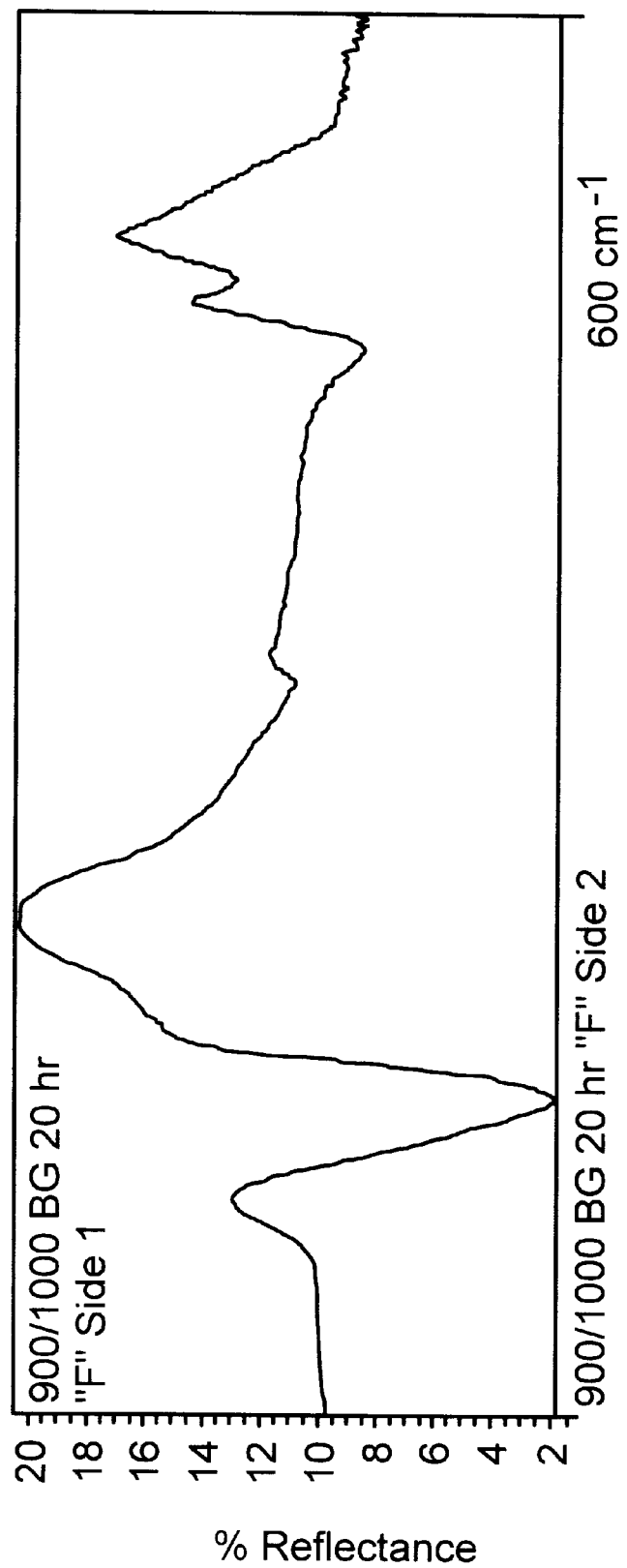
FIG. 2. Reproduction of a FTIR spectra for twice sintered (900° C. and 1000° C.) 45S5 BIOGLASS® (brand of bioactive glass) discs after reacting for 20 hours.

Referring to FIG. 1(a), FIG. 1(b), and FIG. 2. in a typical FTIR scan of bioactive glass soaked in SBF, hydroxyapatite peaks are located near 550 and 610 $cm^{-1}$, whereas the peak near 450 $cm^{-1}$ is attributed to the hydrated silica layer which forms upon immersion. This silica peak near 450 $cm^{-1}$ decreases as the hydroxyapatite layer grows. The in vitro ability of the discs to form hydroxyapatite layers appears to be greater with increasing sintering temperature. The figures show FTIR scans for bioactive glass discs (I cm diameter by 2–3 mM thick) soaked in simulated body fluid for 0–24 hours. FIG. 1a shows the FTIR spectra for bioactive glass laminate sintered at 1000° C. for 3 hr prior to submersion in SBF. The spectra after 24 hours immersion is shown in FIG. 1b. Hydroxyapatite peaks are seen at approximately 600 $cm^{-1}$. The greatest bioactive response was observed for a bioactive glass sample sintered twice (900° and 1000° C. for 3 hours each).

The FTIR spectra for an unreacted bioactive glass disc hot pressed under vacuum closely resembled FIG. 1(a). Therefore it is hypothesized that the bioactive glass is not reduced under vacuum processing and retains in vitro bioactivity.

Mechanical Properties

Strength indentation methods ( e.g., Vickers diamond, 0.5 kg load) are used to determine the flexural strength and fracture toughness of the laminates by four point bend testing. Sample dimensions are determined by ASTM Standard C 1161-90 (1–5 mm thick, 2 mm wide, and 25 mm length). The inner span of the 4-point test apparatus is 6.67 mm and the outer span 19.9 mm. Both the tensile and compressive side of the sample are polished with diamond wheels. The tensile side is further polished with diamond paste. The tensile side corners are also rounded to avoid stress concentrations. The sample is pre-indented with a diamond indentor. The samples are then loaded in a tensile testing machine at a rate of 0.1 mm/min to fracture.

The bulk and true density of s samples may be measured ed as function of the processing conditions (temperature, pressure and atmosphere) using gas pycnometry. Young's modulus may be determined using ultrasonic methods . Mechanical testing includes cutting and polishing samples, and performing four point bend testing according to ASTM C 1161-90 [281]. Strength data is analyzed using the Studentist test and/or the combination of ANOVA and Fisher's least significant difference test.

Characterization

XRD was performed on as-received ed 45S5 BIO-GLASS® powder and on two sintered samples (600 and 900° C.). Crystallinity was minimal in the as-received samples and increased with sintering temperature.

SEM analysis has revealed that significant porosity may develop both within the bulk and on the surface of 45S5 BIOGLASS® discs sintered at >900° C. A second high temperature sintering also tends to lead to more pronounced porosity development. Pores may be as large as 100 microns and tend to be rounded suggesting loss of volatiles. As bioactivity testing has revealed, the discs are bioactive and therefore the glass is not likely loosing Na+. Furthermore, the glass is initially pored at 1300–1 350° C. so the glass should remain stable at these lower temperatures. The most likely source of loss is water present as OH groups. FTIR spectroscopy has shown the presence of large OH peaks near 3400 $cm^{-1}$ in tape cast laminates. Water may be lost continuously from the start of heating. However, as densification begins near 900–1000° C., the loss may only become noticeable at this temperature. Water may break apart Si—O—Si links, making the glass more amenable to forming HA on the surface, despite the high crystallinity of the 34S5 BIOGLASS® sintered at 900–1000° C.

The amount of crystallization in 45S5 BIOGLASS® laminates will be determined as a function of temperature so that the optimum processing conditions with 316L steel and titanium can be used.

The 316L stainless steel is quite oxidation resistant, however, burnout does introduce some oxide onto the surface. Therefore, the steel is expected to bond well with the 45S5 BIOGLASS® laminates to produce a composite with high toughness. The higher thermal expansion coefficient of the steel will place the outer 45S5 BIOGLASS® layers in residual compression which should further increase the apparent fracture toughness. Titanium is the most challenging of the metals, because of its high melting temperature of approximately 1670° C.

Three point bend testing (14 mm span, 0.1 mm/min loading rate) was performed on as processed beams sintered at 900° C. (3 hrs). The beams are fractured by the application of a force in the center of the beam on one side while the beam is supported at the two ends on the opposite side. The average fracture stress was 71 MPa (n=5) with a standard deviation of 3.7. The 4 point bend results for a second batch of beams sintered at 900° C. were evaluated. The hardness was 2.8 GPa (Vicker's indentation method). The density was 2.73 g/cc, as determined by gas pycnometry.

The laminate can be used for bone fracture fixation. Bone plates are used to hold ends of the bone in close proximity so that healing can take place. Flat bone plates can easily be produced by tape casting methods. Currently, bone plates are fabricated from metals or polymers, materials which are not bioactive. A bioactive material should aid the healing response.

We claim:

1. A bioactive composite material comprising an outer layer of bioactive, glass, an interlayer, and a layer of ductile metal, the interlayer being intermediate to the outer layer of bioactive glass and the layer of metal, wherein the composite material has a second layer of ductile metal.

2. A method of replacing bone material comprising contacting bone in need thereof with the composition of claim 1.

3. A bioactive composite material comprising bioactive glass reinforced with at least two ductile, metallic layers.

4. The material of claim 3, wherein the composite material is a laminate.

5. The material of claim 3, wherein the composite material has a flexural strength equal to or greater than 100 MPa and fracture toughness of greater than 5 MPa m$^{1/2}$.

6. The material of claim 3, wherein the metal of the metallic layer is stainless steel, titanium, nickel or aluminum.

7. The material of claim 6, wherein the metal of the metallic layer is stainless steel.

8. The material of claim 3, wherein the composite further comprises layers of alumina, porous alumina, hydroxyapatite, metal, or thereof.

9. The material of claim 3, wherein the bioactive glass is composed of the following compounds by percent weight:

| Compound | Percent |
| --- | --- |
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5. |

10. The material of claim 9, wherein the compounds are combined in the following proportions by percent weight:

| Compound | Percent |
| --- | --- |
| $SiO_2$ | 45 |
| CaO | 24.5 |
| $Na_2O$ | 24.5 |
| $P_2O_5$ | 6. |

11. A method of replacing bone material comprising contacting bone in need thereof with the composition of claim 3.

12. The composite material of claim 3, wherein said composite is in the form of a multi-layered tape.

* * * * *